United States Patent
Johe

(10) Patent No.: US 10,322,115 B2
(45) Date of Patent: Jun. 18, 2019

(54) AMELIORATION OF NEURAL DEFICITS ASSOCIATED WITH DIABETES

(71) Applicant: Neuralstem, Inc., Germantown, MD (US)

(72) Inventor: Karl K. Johe, Hallandale Beach, FL (US)

(73) Assignee: Neuralstem, Inc., Germantown, MD (US)

( * ) Notice: Subject to any disclaimer, the term of this patent is extended or adjusted under 35 U.S.C. 154(b) by 0 days.

(21) Appl. No.: 15/702,162

(22) Filed: Sep. 12, 2017

(65) Prior Publication Data

US 2018/0071267 A1  Mar. 15, 2018

Related U.S. Application Data

(60) Provisional application No. 62/393,514, filed on Sep. 12, 2016.

(51) Int. Cl.
| | |
|---|---|
| *A61K 31/44* | (2006.01) |
| *A61P 25/00* | (2006.01) |
| *A61P 25/02* | (2006.01) |
| *A61K 31/437* | (2006.01) |
| *A61K 31/444* | (2006.01) |
| *A61K 31/455* | (2006.01) |
| *A61K 31/496* | (2006.01) |
| *A61K 31/4439* | (2006.01) |

(52) U.S. Cl.
CPC ............ *A61K 31/437* (2013.01); *A61K 31/44* (2013.01); *A61K 31/444* (2013.01); *A61K 31/4439* (2013.01); *A61K 31/455* (2013.01); *A61K 31/496* (2013.01); *A61P 25/00* (2018.01); *A61P 25/02* (2018.01)

(58) Field of Classification Search
CPC .. A61K 31/437; A61K 31/444; A61K 31/496; A61K 31/44; A61K 31/4439; A61K 31/455; A61P 25/00; A61P 25/02
USPC .......... 514/253, 253.01, 332, 352; 546/279.1
See application file for complete search history.

(56) References Cited

U.S. PATENT DOCUMENTS

| | | | |
|---|---|---|---|
| 7,125,898 B2 | 10/2006 | Aston et al. | |
| 7,560,553 B1 * | 7/2009 | Kelleher-Andersson | G01N 33/5008 544/365 |
| 7,858,628 B2 * | 12/2010 | Kelleher-Andersson | G01N 33/5008 514/253.01 |
| 8,030,492 B2 * | 10/2011 | Kelleher-Andersson | G01N 33/5008 546/121 |
| 8,058,434 B2 * | 11/2011 | Kelleher-Andersson | G01N 33/5008 544/323 |
| 8,362,262 B2 * | 1/2013 | Kelleher-Andersson | G01N 33/5008 546/279.1 |
| 8,674,098 B2 * | 3/2014 | Kelleher-Andersson | G01N 33/5008 544/350 |
| 8,846,914 B2 * | 9/2014 | Kelleher-Andersson | G01N 33/5008 544/323 |
| 9,572,807 B2 * | 2/2017 | Johe | A61K 31/496 |

FOREIGN PATENT DOCUMENTS

| | | |
|---|---|---|
| WO | WO-2015/144976 | 10/2015 |
| WO | WO-2015/195567 | 12/2015 |

OTHER PUBLICATIONS

International Search Report and Written Opinion for PCT/US17/50312, dated Nov. 13, 2017, 9 pages.

Stevens et al., "Nicotinamide Reverses Neurological and Neurovascular Deficits in Streptozotocin Diabetic Rats," The Journal of Pharmacology and Experimental Therapeutics (2007) 320(1):458-464.

Sun et al., "Gastrodin Inhibits Allodynia and Hyperalgesia in Painful Diabetic Neuropathy Rats by Decreasing Excitability of Nociceptive Primary Sensory Neurons," PloS ONE (2012) 7(6):e39647, 15 pages.

* cited by examiner

*Primary Examiner* — My-Chau T. Tran

(74) *Attorney, Agent, or Firm* — Morrison & Foerster LLP

(57) ABSTRACT

Methods for treating non-systemic deficiencies associated with diabetes using 2-amino substituted nicotinamides or their pharmaceutically acceptable salts.

4 Claims, No Drawings

AMELIORATION OF NEURAL DEFICITS ASSOCIATED WITH DIABETES

CROSS-REFERENCE TO RELATED APPLICATIONS

This application claims priority from U.S. provisional application 62/393,514 filed 12 Sep. 2016. The disclosures of which are herein incorporated by reference in their entirety.

TECHNICAL FIELD

The invention relates to treatment of diabetic subjects with compounds that ameliorate the non-systemic deficits associated with diabetes. More particularly, it concerns the use of 2-amino substituted nicotinamides for this purpose.

BACKGROUND ART

Diabetes among both children and adults is becoming increasingly common in industrialized societies. Type I diabetes occurs most frequently in children and is associated with the inability of the pancreas to provide insulin as a result of an immune system attack on insulin-producing cells. Type II diabetes occurs most frequently in adults and is associated with insulin resistance such that the pancreas cannot produce sufficient insulin to provide the mechanism for glucose metabolism. Diabetes is associated with a complex pattern of negative consequences in addition to the direct physiological result of hyperglycemia and increased levels of glycated haemoglobin (HbA1c). These systemic indices of diabetes are often accompanied by additional deficits, including thermal hypoalgesia, pathology of small fibers, including those associated with the corneal nerves and sensory fibers in the dermis, and mental deficits due to nerve damage.

A family of U.S. granted patents, represented by, for example, U.S. Pat. No. 8,362,262, discloses low molecular weight compounds that are capable of stimulating neuronal growth. Subsequently, it was found that certain 2-amino-substituted nicotinamides were useful in treating depression, in particular, major depressive disorder in humans as described in PCT publication WO2015/195567. The negative deficits associated with diabetes, however, especially those associated with neural aberrations, are not addressed by these documents.

DISCLOSURE OF THE INVENTION

It has now been found that certain 2-amino-substituted nicotinamides are especially useful in prevention or repair of various aspects of negative sequelae of both Type I and Type II diabetes.

Accordingly, in one aspect, the invention is directed to a method to ameliorate the non-systemic deficiencies associated with diabetes by administering to a subject in need of such amelioration, a pharmaceutical composition wherein the active ingredient is a 2-amino-substituted nicotinamide or a pharmaceutically acceptable salt thereof. In particular, the 2-amino-substituted nicotinamide is of the formula:

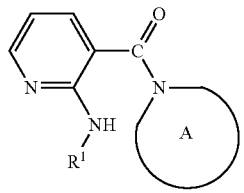

(1)

wherein $R^1$ is an alkyl of 3-8 C and ring A is a 5- or 6-membered saturated ring optionally including an additional nitrogen which is unsubstituted or substituted with an additional nitrogen-containing substituent or a ring-opened form thereof.

Particular exemplified compounds include those of formula (2)

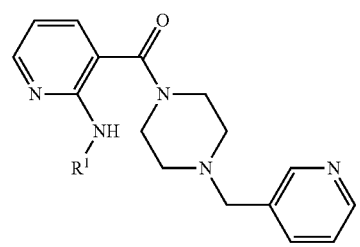

(2)

or formula (3)

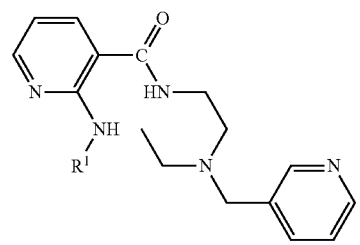

(3)

wherein $R^1$ is a branched alkyl group of 3-5 C or of formula (4)

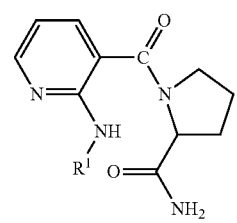

(4)

wherein $R^1$ is an alkyl group comprising a 5- or 6-membered ring.

The invention also includes pharmaceutical compositions and pharmaceutically acceptable salts of the compounds of the invention, in particular phosphate salts thereof.

MODES OF CARRYING OUT THE INVENTION

The methods of the invention are directed to ameliorating the non-systemic deficiencies associated with either Type I or Type II diabetes. "Non-systemic deficiencies of diabetes" as defined herein are those conditions other than the primary hyperglycemia, enhanced glycated haemoglobin (HbA1c) levels and weight loss associated with diabetes. These non-systemic deficiencies include, among others, slowing of motor nerve conduction velocity (MNCV) which is a measure of large motor fiber function, tactile allodynia, thermal response latency which involves small sensory fibers, inferior Barnes maze performance which measures learning and memory and poor performance on object recognition tests.

The list above is not exhaustive, but is typical of measurable deficiencies that are not the primary indicia of diabetes. The non-systemic deficiencies can show up as various symptoms, including loss of eyesight, loss of motor control, and other effects and serious complications such as kidney damage, stroke, heart disease and hypertension. Other complications include neuropathy, gastroparesis, and complications of the foot and skin. These complications are not the primary result of diabetes, but rather secondary sequelae that the method of the invention is designed to ameliorate.

The active agents useful in the method of the invention have the general formula (1) noted above wherein $R^1$ is an alkyl of 3-8 C and ring A is a 5- or 6-membered saturated ring optionally including an additional nitrogen or a ring-opened form thereof. Thus, $R^1$ may be, in formula (1), a straight or branched chain alkyl group of at least 3 C, such as isopropyl, secondary butyl, n-butyl, isoamyl, sec-amyl, hexyl, isohexyl and the like or comprise a saturated ring. Preferably in formula (2) or (3), $R^1$ is a branched alkyl of 3-5 C, in particular isoamyl and, in formula (4), $R^1$ comprises a 5- or 6-membered saturated ring. Preferred embodiments of ring A are a piperidine or piperazine ring or ring opened forms thereof or a pyrrolidine ring. Typically, ring A is substituted with at least an additional nitrogen-containing substituent, including a substituent including an additional pyridine ring such as pyridyl methyl, or pyridyl ethyl or is a simpler substituent such as a carboxamide. Preferred forms of ring A are shown in formulas (2), (3) and (4) above along with appropriate substituents.

The compounds of the invention are formulated in standard pharmaceutical formulations such as those found in *Remington's Pharmaceutical Sciences*, latest edition, Mack Publishing Co., Easton, Pa. and include formulations for oral administration and parenteral administration. Typically, the compounds are administered orally in the form of tablets, capsules or in formulations that are administered as syrups or any other standard formulation. In some instances, the formulations may be designed for delayed release or may be designed for more instantaneous delivery. A variety of formulations that would be suitable for the compounds of the invention is known in the art and is subject to the decision of the practitioner with regard to route of administration.

Dosage levels also depend on the judgment of the practitioner, but are generally in the range of 0.01 mg/kg to 1-2 g/kg.

In general, the subjects of the treatment will be humans, although it is useful to employ laboratory animals as well in order to assess appropriate dosages, routes of administration and formulations. Thus, the subjects of the invention include not only humans, but laboratory research animals such as rabbits, rats, mice and the like. In some instances, other mammalian subjects may be appropriate such as in veterinary contexts where the subject may be ovine, bovine or equine or the subject may be a companion animal such as dog or cat.

The compounds of the invention may be administered in the form of their pharmaceutically acceptable salts such as halides, maleates, succinates, nitrates and the like. Particularly favored are phosphate salts.

The frequency of administration and dosage schedules is also dependent on the practitioner and the dose may be chronic and on a daily basis, weekly basis or more frequent, or a single dosage may suffice. The compounds of the invention may also be administered in combination with other active agents either in the same composition or sequentially.

The following examples illustrate, but do not limit the invention,

Example 1

Effect of Test Compounds on Type I Diabetes Model

Adult female Swiss Webster mice (20-25 grams) were used in the study. They were maintained in a room at 65-82° F. and relative humidity of 30-70% illuminated with fluorescent lighting on a 12 hour light/dark cycle. The animals were maintained 2-3 per cage with free access to dry food and municipal water. Diabetes was induced following an overnight fast by injection of streptozotocin (STZ) (90 mg/kg ip in 0.9% sterile saline) on two consecutive days. Hyperglycemia was confirmed 4 days later in a sample of blood obtained by tail prick using a strip operated reflectance meter. Animals were observed daily and weighed weekly during the study period.

Test compounds were evaluated, with treatment begun immediately after onset of diabetes (Part A) or after 7-8 weeks of diabetes in Part B. Each group started with 10 animals per group to allow identification of differences in nerve conduction, paw thermal latency and intra-epidermal nerve fiber (IENF) density between control and diabetic mice, assuming the routinely observed 20-40% difference between groups and measurement coefficients of variation of 10-20%.

PART A (onset)
Control+vehicle
Diabetic+vehicle
Diabetic+insulin (by implanted pellet)
Diabetic+NSI-158
Diabetic+NSI-189
Diabetic+NSI-190
PART B (7-8 weeks)
Control+vehicle
Diabetic+vehicle
Diabetic+NSI-150
Diabetic+NSI-182
Diabetic+NSI-183
Diabetic+NSI-189

Insulin was supplied by an implanted insulin pellet replaced monthly as needed (LinBit™, LinShin, Canada) and the test compounds were supplied by oral gavage. The following measurements were made 24 hours after delivery of test compound:
Body weight: Weekly from onset of diabetes;
Blood glucose: At onset of diabetes and monthly thereafter;

MNCV (large motor fiber function): Before onset of diabetes and monthly thereafter;

Paw tactile response threshold (large sensory fiber function) by manual von Frey filament: Monthly from onset of diabetes;

Paw thermal response latency (small sensory fiber): Monthly from onset of diabetes;

Corneal nerve density (small sensory fiber structure): Images were collected before onset of diabetes and monthly thereafter;

Barnes maze performance (learning and memory): After 10 weeks of diabetes and at study termination; and Object recognition test (memory): After 10 weeks of diabetes and at study termination.

Paw skin tissue was evaluated for IENF density in some cases.

The various procedures set forth above are those described in the art as follows:

Jolivalt, C. G., et al., *Exp. Neurol.* (2010) 223:422-431;

Jolivalt, C. G., et al., *Diabetes Obes. Metab.* (2011) 13:990-1000;

Jolivalt, C. G., et al., *Neuroscience* (2012) 202:405-412; and

Chen, D. K., et al., *J. Peripher. Nerv. Syst.* (2013) 18:306-315.

As expected, STZ injection attenuated weight gain and induced hyperglycemia and enhanced terminal HbA1c levels as indicative of Type I diabetes. Insulin treatment which was administered in Part A from the outset partially restored weight gain, reduced hyperglycemia and reduced HbA1c levels. None of these systemic indices were altered by treatment with any test compound.

The agents tested are as follows:

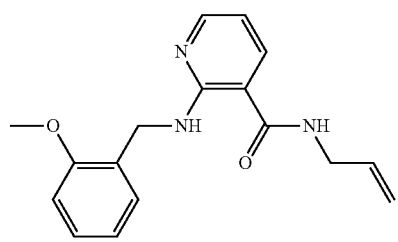
NSI-150

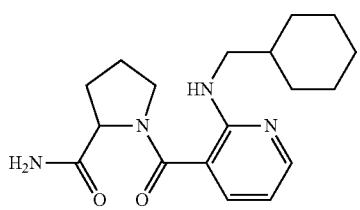
NSI-158

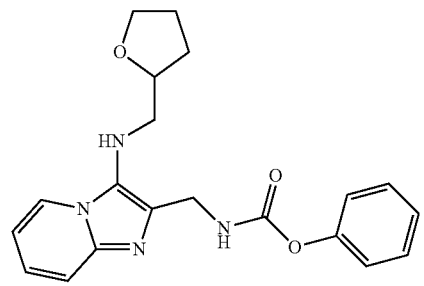
NSI-182

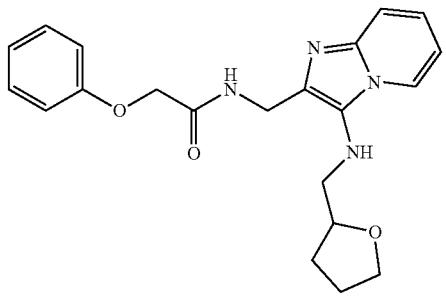
NSI-183

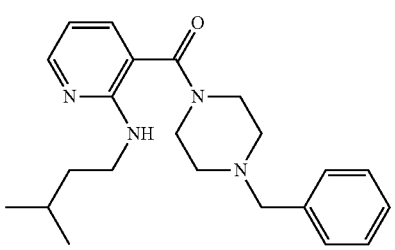
NSI-189

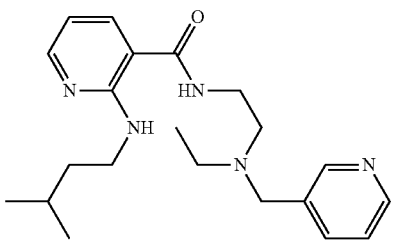
NSI-190

The results were as follows:

MNCV: in this non-systemic index, the diabetic mice develop progressive MNCV slowing as shown in both Parts A and B which was prevented in Part A by administration of insulin. In Part A, agents NSI-158, NSI-189 and NSI-190 produced mild attenuation of MNCV slowing at the end of the study period, but test agents NSI-150, NSI-182 and NSI-183 did not. In Part B, NSI-189 partially reversed MNCV slowing.

Paw tactile allodynia: The diabetic mice as expected developed tactile allodynia within 4 weeks from diabetic onset which was attenuated by insulin treatment. Test agents NSI-158, NSI-189 and NSI-190 in Part A attenuated tactile allodynia when measured 24 hours after the last treatment, but test agents NSI-150, NSI-182 and NSI-183 in Part B did not. In Part B, NSI-189 partially reversed paw tactile allodynia.

Paw response to heat: Diabetic mice develop paw thermal hypoalgesia 8-12 weeks after onset of diabetes but insulin, as expected, prevents this. In Part A, test agents NSI-158, NSI-189 and NSI-190 prevented paw thermal hypoalgesia but in Part B test agents NSI-150, NSI-182 and NSI-183 did not. In Part B, NSI-189 prevented progression of paw thermal hypoalgesia.

Small fiber pathology: A number of aspects of small fiber pathology were studied, including corneal nerve density in Bowman's layer and in the stroma which were significantly reduced in diabetic mice, wherein the loss of distal regions of the trigeminal nerve-derived small sensory fibers was prevented by insulin as was this loss in more proximal regions. In Part A, only NSI-189 attenuated the loss in Bowman's layer and NSI-189 and NSI-190 attenuated this loss in the stroma. However, there was no protective effect in Part A by NSI-158 and NSI-190 with respect to Bowman's layer. In Part B, NSI-189 was protective both in Bowman's layer and in stroma but there was no protective effect in the stroma in Part B by NSI-150, NSI-182 or NSI-183. However, in Part B, NSI-182 and NSI-183 were protective in Bowman's layer.

Nerve density in the sub-epidermal nerve plexus: This was reduced in diabetic mice and prevented by insulin treatment. In Part A it was attenuated by NSI-158, NSI-189 and NSI-190 and in Part B only NSI-189 was protective.

IENF density in isolated tissue: A reduction of this density in diabetic mice was prevented by insulin treatment and attenuated in Part A only by NSI-189 and NSI-158 and reversed in Part B only by NSI-189.

Object Recognition: Diabetic mice showed impaired short-term memory at weeks 10 and 16 but this was not prevented by systemic insulin. In Part A, only NSI-190 prevented this memory loss and none of the agents in Part B were successful.

Barnes maze test: Diabetic mice showed impaired initial acquisition, but reinforced learning and short-term retention were normal altogether long-term retention was impaired. Insulin treatment prevented all of this. All of the test agents, NSI-158, NSI-189 and NSI-190 in Part A improved long-term retention without altering the other parameters, while the agents tested in Part B were not successful.

Example 2

Type II Diabetes

Type II diabetes was modeled by db/db (BKS.Cg-Dock7$^m$+/+Lepr$^{db}$/J) mice. These mice were maintained in a manner similar to that set forth in Example 1. The progressive development of MNCV slowing, tactile allodynia and thermal hypoalgesia was significantly reversed by NSI-189 after 17-22 weeks of treatment.

The invention claimed is:
1. A method to ameliorate non-systemic deficiencies associated with Type I and/or Type II diabetes, which method comprises administering to a human subject diagnosed with Type I or Type II diabetes an effective amount of a 2-amino substituted nicotinamide or a pharmaceutically acceptable salt thereof,
wherein the 2-amino substituted nicotinamide is of the formula

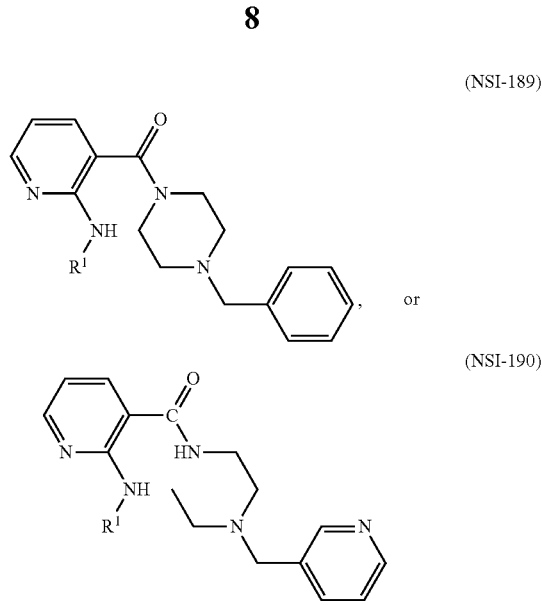

wherein R$^1$ is isoamyl, and
wherein the non-systemic deficiency is slowing of MNCV, tactile allodynia, thermal hypoalgesia, small fiber pathology or short or long-term memory loss.
2. The method of claim 1, wherein the 2-amino substituted nicotinamide is of the formula

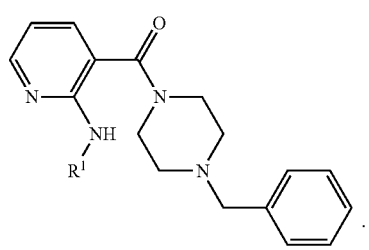

3. The method of claim 1 wherein the 2-amino substituted nicotinamide is in the form of a phosphate salt.
4. The method of claim 1 which further includes subsequent testing of said subject for amelioration of slowing of MNCV, tactile allodynia, thermal hypoalgesia, small fiber pathology, or short or long-term memory loss.

* * * * *